United States Patent
Eckhardt et al.

(12) 
(10) Patent No.: US 6,383,279 B1
(45) Date of Patent: *May 7, 2002

(54) DENTAL IMPRESSION COMPOSITION ON FUNCTIONALIZED POLYETHERS

(75) Inventors: Gunther Eckhardt, Frieding; Erich Wanek, Kaufering; Guenther Lechner, Woerthsee; Peter Bissinger, Mering; Markus Mikulla, Frieding, all of (DE)

(73) Assignee: ESPE Dental AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/151,290

(22) Filed: Sep. 11, 1998

(30) Foreign Application Priority Data

Sep. 12, 1997 (DE) .......................... 197 40 234

(51) Int. Cl.⁷ .......................... A61C 9/00; C08G 65/08; C08G 65/20; C08G 65/32
(52) U.S. Cl. ...................... 106/38.2; 528/405; 528/417; 433/214
(58) Field of Search ................ 528/405, 417; 106/38.2; 433/214

(56) References Cited

U.S. PATENT DOCUMENTS

| | | | | |
|---|---|---|---|---|
| 3,453,242 A | * | 7/1969 | Schmitt et al. | 528/322 |
| 4,493,911 A | * | 1/1985 | Schmitt et al. | 524/724 |
| 4,500,705 A | | 2/1985 | Copelin | 528/417 |
| 4,638,097 A | * | 1/1987 | Mueller | 568/617 |
| 4,762,951 A | * | 8/1988 | Mueller | 528/417 |
| 4,933,503 A | * | 6/1990 | Mueller | 568/621 |
| 5,130,348 A | * | 7/1992 | Zahler et al. | 528/424 |
| 5,179,186 A | * | 1/1993 | Muller et al. | 528/49 |

FOREIGN PATENT DOCUMENTS

| | | |
|---|---|---|
| DE | 3246654 A1 | 6/1984 |
| DE | 3730088 * | 3/1989 |
| DE | 4406858 * | 9/1995 |
| WO | 96/13538 | 5/1996 |

* cited by examiner

*Primary Examiner*—Robert E. L. Sellers
(74) *Attorney, Agent, or Firm*—Birch Stewart Kolasch & Birch LLP

(57) ABSTRACT

A dental impression composition comprises a polyether derivative functionalized via the hydroxyl groups of a polyether polyol with groups such as aziridine, epoxide and unsaturated substituents including (meth)acrylic, allyl, vinyl, vinyl ether or maleate groups, wherein the level of cyclic oligomeric polyethers is less than 5.0 weight percent.

6 Claims, No Drawings

DENTAL IMPRESSION COMPOSITION ON FUNCTIONALIZED POLYETHERS

FIELD OF THE INVENTION

The invention relates to dental compositions on the basis of polyether derivatives, to their preparation and to their use as impression materials.

BRIEF DESCRIPTION OF THE CONVENTIONAL ART

The preparation of polyether derivatives and their use in dental materials has long been known. Thus, for example, DE-C-1 745 810 describes the preparation of mouldings on the basis of aziridino polyethers.

The use of aziridino polyethers in polyether impression compositions is described in patent specifications DE-C-3 246 654, EP-A-0 421 371 and EP-A-0 110 429. EP-A-0 460 478 describes light-curing impression materials on the basis of polyether urethane acrylates.

To take impressions of the concrete conditions in the patient's mouth with the help of suitable impression compositions is the prerequisite for the preparation of precisely fitting denture sets, crowns and bridges, inlays and onlays.

Of the known impression compositions, the compositions based on polyether derivatives are characterized by their hydrophilic character, which makes possible a very high precision of the impressions.

However, a disadvantage of these compositions is that they cannot be demoulded too easily. In other words, the demouldability of the copy when the impression is taken and the demouldability of the gypsum model after forming the cast of the impression are not satisfactory.

SUMMARY OF THE INVENTION

The object of the present invention is to provide dental compositions on the basis of polyether derivatives which do not display the described disadvantages but are easily demouldable.

This object is achieved by dental compositions on the basis of polyether derivatives which are characterized in that their level of cyclic oligomeric polyethers is smaller than 5.0, preferably smaller than 0.9 wt.-%.

Surprisingly, it was found within the framework of the present invention that the cyclic polyether oligomers present in the polyether compositions are responsible for the compositions displaying a poor demouldability of the copy when the impression is taken and a poor demouldability of the gypsum model after forming the cast of the impression.

DETAILED DESCRIPTION OF INVENTION

The basis for the polyether derivatives used in dental materials is polyether polyols which can be prepared by different polymerization processes and generally have molar masses in the range from 500 to 10,000 g/mol.

It is already known (G. Pruckmayr et al., ACS Symp. Ser. 172, (1981), pp. 197 to 203) that, during the preparation of polyether glycols by homopolymerization of tetrahydrofuran or ethylene oxide or by copolymerization of tetrahydrofuran with ethylene oxide under the catalytic action of strong acids, cyclic oligomers form as well as linear polyethylene glycols and that the level of such cyclic oligomers can be up to 20 wt.-% depending on the reaction conditions (DE-A-3 514 547) and is usually below 10 wt.-% in the case of industrial polyether polyols.

These cyclic oligomers have different ring sizes and/or different ratios of the incorporated monomer units depending on the comonomer composition and the reaction conditions.

Processes which relate to the removal of the cyclic oligomers are also described in the state of the art. Thus EP-A-0 153 794 describes the removal of the cyclic oligomers through extraction by means of heptane.

Extraction processes for the removal of the cyclic oligomers are also described in DE-A-3 514 547, DE-A-3 607 946 and DE-A-3 730 888.

A three-phase extraction with upstream vacuum distillation in a short-path evaporator is proposed according to EP-A-0 305 853.

Low-odour, higher-molecular-weight polyether polyols which are purified by adding water at temperatures of 110 to 150° C. and under reduced pressure are described in DE-A-195 30 388. This purification process leads to a reduction in the level of odour-intensive compounds and makes the polyethers purified in this way suitable for the preparation of low-emission polymers, cosmetics and pharmaceutical products building on polyether polyols.

In the case of dental compositions the removal of the cyclic oligomers has not been considered thus far, since these dental compositions display excellent properties and thus there was no need to remove the cyclic oligomers. Surprisingly, as already mentioned above, it was found within the framework of the invention that the difficulty in demoulding the polyether compositions is to be attributed to the presence of the cyclic oligomers. Through their removal, dental compositions on polyether basis are obtained which possess an impression precision which remains good, but are also easily demouldable at the same time.

With a pre-set incorporation ratio of the monomers, the overall level of cyclic oligomeric polyethers, the incidence of the individual types relative to one another and thus the molar mass distribution of the cyclic oligomers can be influenced through the reaction temperature and the realized concentration pattern of the monomers via the reaction time.

The analytical determination of the level of cyclic oligomeric polyethers and the incidence of the individual oligomer types can be realized by means of gas chromatography with a FID detector or in GC-MS coupling.

The removal of the cyclic oligomeric polyethers can take place both at the process stage of the polyether polyols and after their functionalization with aziridino groups, double-bond-containing groups and epoxide groups, methods based on distillation and extraction or membrane separation being usable.

The separation methods based on distillation are associated with the application of high temperatures and thus the dangers of thermal damage. Thus, the polyether polyols which are cleaned up by means of distillation can have an odour which is unpleasant in most cases.

The distillation-based purification of the already functionalized polyether polyols is difficult to carry out on account of the danger of premature polymerization. Extraction with hydrocarbons having 4 to 12 C atoms is suitable in principle for the extraction-based removal of the cyclic oligomeric polyethers. The extraction can be carried out continuously or batchwise according to the known liquid/liquid separation methods (see Ullmann's Encyclopedia of Industrial Chemistry, 5$^{th}$ Edition, Volume B3: Unit Operations). The extraction-based removal of the cyclic oligomeric polyethers by means of hydrocarbons is possible both at the stage of the polyether polyols and following the functionalization. It has proved advantageous, during the preparation of polyether derivatives for use in dental materials, to combine the purification stage of the removal of the cyclic material through extraction with the purification stages after the functionalization.

The polyether polyols used for the functionalization are preferably prepared by copolymerization of tetrahydrofuran and ethylene oxide in the molar ratio 10:1 to 1:1 and preferably 5:1 to 3:1 in the presence of strong acid, such as for example boron fluoride etherates.

It is also possible to use, for the functionalization, polyether polyols which, in addition to tetrahydrofuran units, also contain ethylene oxide units and or propylene oxide units.

The polyether polyols possess at least 2 hydroxyl groups, but can also contain up to 20 hydroxyl groups per molecule.

The molar masses ($M_n$) of the polyether polyols used for the functionalization lie in the range from 500 to 20,000 and preferably in the range from 2,000 to 10,000 g/mol. The functionalization with aziridino groups can take place for example according to the method described in DE-C-1 745 810.

A functionalization with epoxide groups, such as for example 3,4-epoxycyclohexyl groups, is possible according to the teaching of DE-A-195 34 668. The functionalization with (meth)acrylate groups can take place for example in accordance with DE-A-4 406 858, Example 1. The known methods of conversion of primary alcohols can be used for the functionalization with allyl groups, vinyl groups, vinyl ether groups and maleate groups.

Dental compositions which cure through polymer-forming reactions can be manufactured from the functionalized polyether derivatives. Preferred polymer-forming reactions are free radical and cationic polymerization and also hydro-silylation.

The use of the functionalized polyether derivatives which are largely freed of cyclic oligomeric polyethers can take place in very different dental compositions used in dental medicine or dental engineering. Preferred fields of use are single-phase and two-phase dental medicine impression taking and occlusion recording.

The invention is explained further with the aid of the following examples.

EXAMPLES

The preparation of a mixed-polyether dimethacrylate with a low level of cyclic oligomers took place according to Preparation Example 1. Preparation Example 2 describes the preparation of a bis-aziridino polyether with a low level of cyclic oligomeric polyethers, starting from a bis-aziridino-polyether which was obtained in accordance with DE-C-1 745 810.

The determination of the residual level of cyclic oligomeric polyethers in the polyether derivatives of Preparation Examples 1 and 2 took place by means of gas chromatography.

Analysis Method

A Chrompack gas chromatograph (CP 9000) with FID detector was used for the gas chromatographic measurements. The temperature of the detector block was 330° C. A Chrompack 10-m DMS capillary tube was used as column. Hydrogen served as carrier gas, and the carrier gas pressure was 30 kPa. The separations were carried out in a temperature-programmed manner (start 100° C., finish 300° C. rate of increase 20° C./min). In each case 1 microliter of the test solutions (2 wt.-% in dichloromethane) was injected. 15-Krone-5 crown ether (Merck) was added as internal standard. The peak areas were calculated with the help of Turbochrom evaluation software (PE-Nelson). The polyether derivatives of Preparation Examples 1 and 2 were used to prepare the dental materials of Examples 1 to 7.

The removability of the impression was appraised by 2 operators on each of 8 subjects with different denture situations and the subjective impressions were averaged.

The following appraisal system formed the basis for the removability:

1=very good
2=good
3=adequate
4=deficient
5=poor

Preparation Example 1

Preparation of a Mixed-polyether Dimethacrylate with a low Level of Cyclic Oligomers A mixed-polyether diol with a molar mass ($M_n$) of 6500, prepared by cationic copolymerization of ethylene oxide and tetrahydrofuran in the molar ratio 1:3, was converted into the mixed-polyether dimethacrylate through reaction with methacrylic acid anhydride with catalytic action of potassium hydroxide analogously to the procedure described in DE-A-4 406 858, Example 1.

The reaction mixture was set at neutral accompanied by stirring by adding a 2% aqueous solution of potassium hydroxide. The two-phase mixture was covered with heptane and the three-phase mixture stirred for 2 hours at 10° C. After removal of the heptane phase the mixture was covered afresh with heptane. This procedure was repeated 3 times and then the heptane phase and the aqueous phase were separated off.

The residual water was removed from the middle phase after the addition of 200 ppm 4-methoxyphenol by vacuum distillation at 50° C.

The obtained mixed-polyether dimethacrylate was colourless and had a double bond equivalent mass of 3420 g/mol.

The level of cyclic polyether oligomers, measured by the described gas chromatographic method, was 0.09 wt.-%.

Preparation Example 2

Preparation of an Aziridino Polyether Free of Cyclic Material 500 parts by weight of an aziridino polyether, prepared according to the teaching of DE-C-1 745 810, with a numerically average molar mass of 6100 g/mol and an incorporation ratio of ethylene oxide to tetrahydrofuran units of 1:3.6, containing 8.2 parts by weight of cyclic oligomeric polyethers, which had been washed with water 5 times after the functionalization with aziridino groups, was covered with 300 parts by weight hexane without intermediate drying and stirred at 20° C. The upper phase (hexane phase) was removed and the residue covered afresh with 300 parts by weight hexane.

This process was repeated 7 times and then the hexane phase and the aqueous phase were separated off. After working-up of the hexane phase, 450 parts by weight of a bis-aziridino polyether containing 0.25 wt.-% of cyclic oligomeric polyethers were obtained.

Preparation Examples 3 to 5 and Comparative Preparation Example 1

Preparation of the basic components

In each case 100 parts by weight of the basic components were obtained by mixing the preparations characterized below.

| Constituents | Preparation Example 3 Basic paste B1 wt. % | Preparation Example 4 Basic paste B2 wt. % | Preparation Example 5 Basic paste B3 wt. % | Comparative Preparation Example 1 Basic paste VB1 wt. % |
|---|---|---|---|---|
| Aziridino-polyether according to Preparation Example 2 | 57.1 | 53.8 | 51.3 | — |
| Dibenzyltoluene | 12.4 | 13.9 | 16.3 | 11.2 |
| Hydrogenated beef tallow | 14.6 | 15.8 | 15.1 | 14.5 |
| Kieselguhr (diatomaceous earth) | 13.3 | 13.9 | 14.7 | 13.9 |
| Colour pigment | 2.6 | 2.6 | 2.6 | 2.6 |
| Aziridino-polyether, prepared according to DE-C-1 745 810, $M_n$ = 6100 g/mol, incorporation ratio of ethylene oxide to tetrahydrofuran units of 1:3.6; containing 8.2 wt. % of cyclic oligomers | — | — | — | 57.8 |

Preparation Example 6

Preparation of Catalyst Component K 1

32.9 parts by weight of a sulphonium salt which was obtained in accordance with Example 27 of DE-A-2 515 593, 32.0 parts by weight acetyltributylcitrate, 5.8 parts by weight of a block copolymer surfactant consisting of propylene oxide and ethylene oxide with an average molar mass of 6500, 19.1 parts by weight pyrogenic silicic acid, 9.5 parts by weight kieselguhr and 0.7 parts by weight colour pigments were kneaded to produce 100 parts by weight of catalyst paste K1, which is used to cure basic components.

Examples 1 to 3 and Comparative Example 1

Preparation of Impressions

The catalyst components and the basic components were, as given below, mixed on the mixing block in the weight ratio 1:5, the mixtures transferred onto a metal tray and the filled impression tray introduced into the subject's mouth. After a 6-minute residence time in the mouth, calculated from the start of mixing, the impressions were removed.

Composition of the Impression Compositions Mixed in the Ratio 1:5

| | Catalyst paste | Basic paste |
|---|---|---|
| Example 1 | K 1 (as per Preparation Example 6) | B 1 (as per Preparation Example 3) |
| Example 2 | K 1 | B 2 (as per Preparation Example 4) |
| Example 3 | K 1 | B 3 (as per Preparation Example 5) |
| Comparative Example 1 | K 1 | VB 1 (as per Comparative Preparation Example 1) |

The removability of the impressions was assessed in the manner described and is given in the following table.

Results of the Testing of the Compositions According to Examples 1 to 3 and Comparative Example 1

| | Average value "Removability" |
|---|---|
| Example 1 | 2.7 |
| Example 2 | 1.6 |
| Example 3 | 1.3 |
| Comparative Example 1 | 4.3 |

The comparison of the results of the Examples according to the invention with those of Comparative Example 1 shows the superiority of the compositions according to the invention.

Preparation Example 7

Preparation of an Impression Composition 59.3 parts by weight of the mixed-polyether dimethacrylate according to Preparation Example 1 were reacted with 0.9 parts by weight Lucirin TPO (BASF), 30 parts by weight of a urethane dimethacrylate with a double bond equivalent mass of 245 g/mol and 6.1 parts by weight of a multiacrylate with a molar mass of 880 g/mol and a double bond equivalent mass of 250 g/mol and the mixture was made thixotropic by adding 3.7 parts by weight of highly dispersed silicic acid (HDK N20, Wacker).

Example 4

The impression composition obtained in Preparation Example 7 was placed on a plastic tray which has a high transparency, and the filled impression tray was introduced into the subject's mouth.

The radiation of the impression composition took place through the plastic of the impression tray by means a lamp which radiates visible light in the wavelength range from 400 to 500 nm.

The impression was removable after 2½ minutes.

The procedure was carried out on 8 subjects who agreed in describing the taking of the impression as causing only a little stress. Compared with this, the taking of an impression with the impression composition of Comparative Example 1 was described as unpleasant.

What is claimed is:

1. A dental impression composition comprising:

A dental composition comprising functionalized polyether compound derivatives bonded through hydroxyl residues of polyether polyol compounds from which the functionalized polyether compound derivatives are derived, wherein the level of cyclic oligomeric polyethers in the polyether is lower than 5.0 wt. %, and wherein the functionalized polyether compound derivatives contain an aziridino group, and dental surface in a mouth of patient upon which the dental composition is disposed.

2. A dental impression composition according to claim 1, wherein the level of cyclic oligomeric polyethers in the functionalized polyether compound derivatives is smaller than 0.9 wt.-%.

3. A dental impression composition according to claim 1, wherein the level of cyclic oligomeric polyethers with molar masses below 500 g/mol in the functionalized polyether compound derivatives is smaller than 0.5 wt.-%.

4. A dental impression composition according to claim 1, wherein the level of cyclic oligomeric polyethers with molar masses below 350 g/mol in the functionalized polyether compound derivatives is smaller than 0.2 wt.-%.

5. A dental impression composition according to claim 1, wherein the functionalized polyether compound derivatives have been prepared from a polyether polyol which was produced through copolymerization of tetrahydrofuran with ethylene oxide in the presence of strong acids.

6. A dental impression composition according claim 1, wherein the functionalized polyether compound derivatives have been prepared from a polyether polyol which contains tetrahydrofuran units and a member selected from the group consisting of ethylene oxide units, propylene oxide units, and the combination thereof.

* * * * *